(12) United States Patent
Lauchner

(10) Patent No.: US 10,143,486 B2
(45) Date of Patent: Dec. 4, 2018

(54) ULTRASONIC CUTTING DEVICE

(71) Applicant: Medtronic Holding Company Sàrl, Tolochenaz (CH)

(72) Inventor: Craig E. Lauchner, Mountain View, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 328 days.

(21) Appl. No.: 15/043,657

(22) Filed: Feb. 15, 2016

(65) Prior Publication Data

US 2016/0157885 A1 Jun. 9, 2016

Related U.S. Application Data

(62) Division of application No. 13/838,671, filed on Mar. 15, 2013, now Pat. No. 9,289,227.

(51) Int. Cl.
*A61B 17/32* (2006.01)
*A61B 17/16* (2006.01)
*A61B 90/00* (2016.01)

(52) U.S. Cl.
CPC .. *A61B 17/320068* (2013.01); *A61B 17/1671* (2013.01); *A61B 2017/320072* (2013.01); *A61B 2090/08021* (2016.02); *A61B 2217/005* (2013.01); *A61B 2217/007* (2013.01)

(58) Field of Classification Search
CPC ...... A61B 17/320068; A61B 17/32002; A61B 2017/320072; A61B 17/32
See application file for complete search history.

(56) References Cited

U.S. PATENT DOCUMENTS

| | | |
|---|---|---|
| 5,167,619 A | 12/1992 | Wuchinich |
| 5,195,959 A | 3/1993 | Smith |
| 5,314,406 A | 5/1994 | Arias et al. |
| 5,709,698 A | 1/1998 | Adams et al. |
| 6,159,175 A | 12/2000 | Strukel et al. |
| 8,070,765 B2 | 12/2011 | Oliver et al. |
| 2008/0234709 A1 | 9/2008 | Houser |
| 2011/0152759 A1 | 6/2011 | Clymer et al. |
| 2012/0080592 A1* | 4/2012 | Wiseman ........... G01N 35/1095 250/282 |

* cited by examiner

*Primary Examiner* — Victor Nguyen

(57) ABSTRACT

An ultrasonic surgical device for performing a surgical procedure includes an elongated member having a proximal end and a distal end spaced along a longitudinal axis. The elongated member has an inner surface and an outer surface. The inner surface defines a passageway. A septum is configured to separate the passageway into a first conduit and a second conduit. A distal end of the second conduit terminates before a distal end of the first conduit to form a stepped configuration. An ultrasonic-driven cutting blade is disposed within the second conduit and is configured for cutting tissue such that the cutting blade vibrates ultrasonically to cut tissue. The distal end of the first conduit includes an outlet configured for delivering material to a surgical site and the distal end of the second conduit includes an inlet configured for aspirating the surgical site.

20 Claims, 2 Drawing Sheets

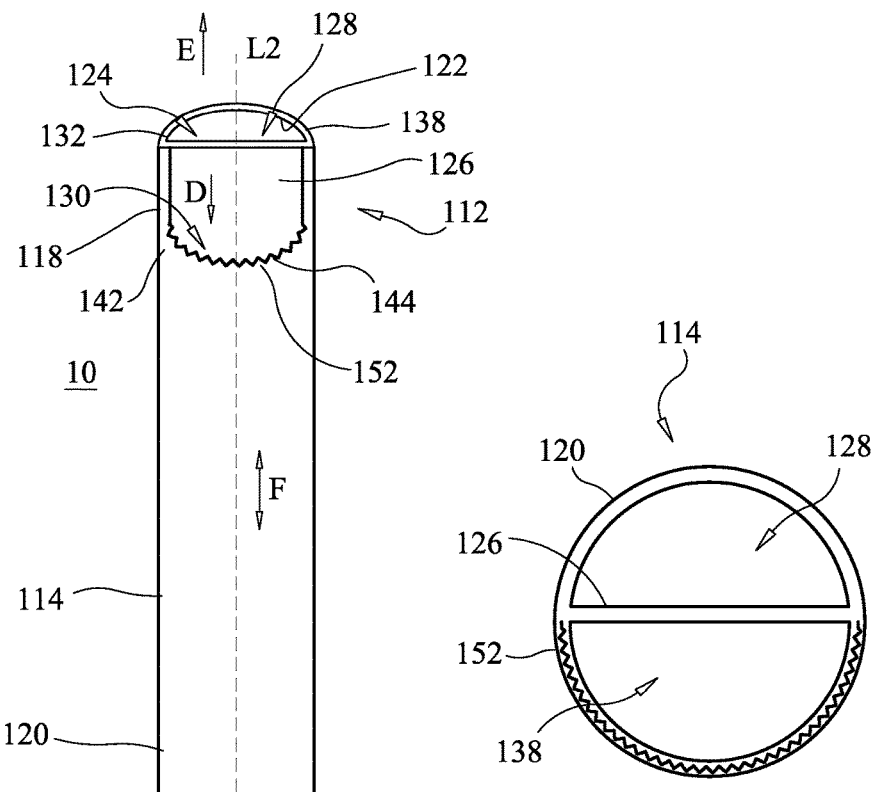
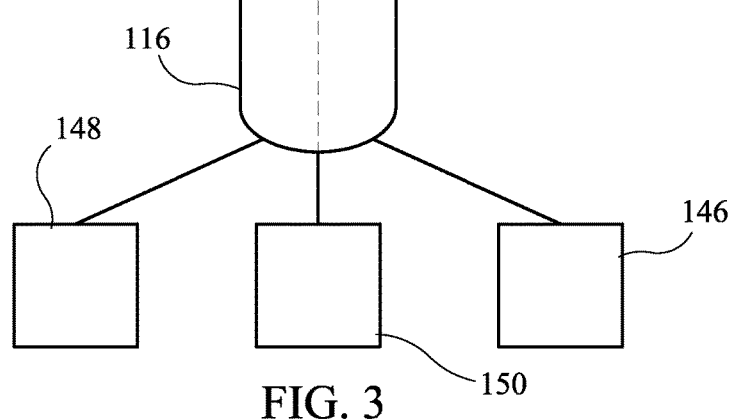
FIG. 3
FIG. 4

ULTRASONIC CUTTING DEVICE

CROSS-REFERENCE TO RELATED APPLICATIONS

This application is a Divisional of U.S. patent application Ser. No. 13/838,671, filed on Mar. 15, 2013, which is incorporated herein by reference herein, in its entirety.

TECHNICAL FIELD

The present invention relates generally to devices and methods for cutting a material or substance. More specifically, the devices and methods are useful for cutting bone while preventing damage to soft tissue.

BACKGROUND

Spinal stenosis typically occurs when the spinal cord, cauda equina and/or nerve root(s) are impinged by one or more tissues in the spine, such as a buckled or thickened ligamentum flavum, hypertrophied facet joints, disc herniations, etc. Impingement of neural and/or neurovascular tissue in the spine by hypertrophied facet joints, disc herniations, etc. may cause pain, numbness and/or loss of strength or mobility in one or both of a patient's lower limbs and/or of the patient's back.

In lumbar spinal stenosis (LSS), such as, for example, central lumbar stenosis or foraminal lumbar stenosis, the space around the spinal cord or nerve roots becomes narrow, thus compressing the spinal cord and the nerve roots. This causes back pain with neurogenic claudication, i.e., pain, numbness, or weakness in the legs that worsens with standing or walking and is alleviated with sitting or leaning forward. Compression of neural elements generally occurs as a result of hypertrophied facet or ligamentum flavum hypertrophy, disc herniations. LSS is one of the most common reasons for back surgery and the most common reason for lumbar spine surgery in adults over 65 years of age. Patients suffering from spinal stenosis are typically first treated with conservative approaches such as exercise therapy, analgesics, anti-inflammatory medications, and epidural steroid injections. When these conservative treatment options fail and symptoms are severe, surgery may be required to remove impinging tissue and decompress the impinged nerve tissue.

Decompressive laminectomy, a well-known treatment for LSS, unroofs the spinal canal by resectioning posterior spinal elements, such as the facet adjacent to the lumbar nerve roots. Wide muscular dissection and retraction is needed to achieve adequate surgical visualization. The extensive resection and injury to the posterior spine and supporting muscles can lead to instability with significant morbidity, both post-operatively and longer-term. Spinal fusion may be required to reduce the resultant instability. Laminectomy may be used for extensive multi-level decompression.

A combination of hemilaminotomy and laminotomy, often referred to as laminoforaminotomy, is less invasive than laminectomy. This procedure focuses on the interlaminar space in order to minimize resectioning of the stabilizing posterior spine. Generally, laminotomy removes the ligamentum flavuum. Muscular dissection and retraction are required to achieve adequate surgical visualization.

Microendoscopic decompressive laminotomy (MEDL) is somewhat similar to laminotomy, but utilizes endoscopic visualization. The position of a tubular working channel is confirmed by fluoroscopic guidance, and serial dilators (METRx™ lumbar endoscopic system, Medtronic) are used to dilate the musculature and expand the fascia. For MEDL, an endoscopic curette, rongeur, and drill are used for the laminotomy, facetectomy, and foraminotomy. The working channel may be repositioned from a single incision for multilevel and bilateral dissections.

Instruments have been developed for effectively cutting and coagulating organic tissue, which employ mechanical vibrations that are transmitted to a surgical end-effector at ultrasonic frequencies. Ultrasonic vibrations, when transmitted to organic tissue at suitable energy levels, and using a suitable end-effector, such as a blade, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, to the surgical end-effector.

Activating or exciting the end-effector, for example, a cutting blade, at ultrasonic frequencies induces longitudinal vibratory movement. High frequency longitudinal or rotational, low amplitude vibrations are used for cutting which produce virtually no heat. The tools used are rated at between about 5 W to about 30 W to assure virtually no heat is produce.

Ultrasonic vibration is induced in the surgical blade by electrically exciting a transducer, for example. The transducer may be constructed of one or more piezoelectric or magnetostrictive elements in the instrument hand piece. Vibrations generated by the transducer section are transmitted to the surgical end-effector or blade via an ultrasonic waveguide extending from the transducer section to the surgical end-effector. The waveguides and the end-effectors are designed to resonate at the same frequency as the transducer. Therefore, when an end-effector is attached to a transducer, the overall system frequency is the same frequency as the transducer itself. However, those skilled in the art will appreciate that the system may be designed where the transducer and the blade resonate at different frequencies and when joined the system resonates at a desired frequency.

Ultrasonic speeds and amplitudes are considered safe for dura material. However, performing spinal surgery, such as, for example, lateral lumbar spinal stenosis decompression ("open decompression") using ultrasonic cutting devices can pose risks to healthy tissues and/or nerves, such as, for example, the lumbar nerve roots because of their cutting capabilities.

Accordingly, there is a need for devices and methods to provide efficient severing or cutting tissue including bone that can be used during a minimally invasive procedure and/or during an open surgical procedure, such as open decompression. Further, there is also a need for devices and methods that provide fine dissection capabilities of bone without damaging nerves. Devices and methods that do not cause a high level of collateral thermal damage and allow for the control of necrosis in the tissue being treated are also needed.

SUMMARY

In one embodiment, in accordance with the principles of the present disclosure, a cutting device is disclosed, which includes an elongated member having a proximal end and a distal end spaced along a longitudinal axis. The elongated member has an inner surface and an outer surface. The inner surface defines a passageway. A septum is configured to separate the passageway into a first conduit and a second conduit. A distal end of the second conduit terminates before a distal end of the first conduit to form a stepped configuration. An ultrasonic-driven cutting blade is disposed within the second conduit and is configured for cutting tissue such that the cutting blade vibrates ultrasonically to cut bone, hard tissue. The distal end of the first conduit includes an outlet configured for delivering material to a surgical site and the distal end of the second conduit includes an inlet configured for aspirating the surgical site.

In one embodiment, in accordance with the principles of the present disclosure, a cutting device is disclosed, which includes an elongated member having a proximal end and a distal end spaced along a longitudinal axis. The elongated member has an inner surface and an outer surface. The inner surface defines a passageway. A lumen, such as, for example, a septum is configured to separate the passageway into a first conduit and a second conduit. A distal end of the second conduit terminates before a distal end of the first conduit to form a stepped configuration. The stepped configuration protects tissue, such as, for example, dura mater when the cutting device is used to cut tissue in or adjacent areas of the body, such as, for example, the spinal cord. That is, the stepped configuration of passageway protects the dura mater when the cutting device is rotated with a hypertrophied facet joint contacting a recessed portion of the cutting device. The distal end of the second conduit has an ultrasonic-driven cutting edge configured for cutting tissue such that the cutting edge vibrates ultrasonically to cut tissue. Vibration protection or shielding, such as, for example, insulation is provided to prevent vibrations from the cutting edge from damaging tissue, such as, for example, dura mater when the cutting device is used to cut tissue in or adjacent areas of the body, such as, for example, the spinal cord. A distal end of the first conduit includes an outlet configured for delivering material to a surgical site and the distal end of the second conduit includes an inlet configured for aspirating the surgical site.

In one embodiment, in accordance with the principles of the present disclosure, a cutting device is disclosed, which includes a tube having a proximal end and a distal end spaced along a longitudinal axis. The tube has an inner surface and an outer surface. The inner surface defines a passageway. A septum is configured to separate the passageway into a first conduit and a second conduit. A distal end of the second conduit terminates before a distal end of the first conduit to form a stepped configuration. A semicircular ultrasonic-driven cutting blade has a serrated cutting edge and is concentrically disposed within the second conduit configured for cutting tissue such that cutting blade vibrates ultrasonically to cut bone. The distal end of the first conduit includes an outlet configured for delivering irrigation fluid to a surgical site and the distal end of the second conduit includes an inlet for aspirating the surgical site. It is envisioned that the first conduit may be smaller than the second conduit. It is further envisioned that the cutting edge may be variously configured and dimensioned, such as, for example, blunt, round or serrated, depending upon the requirements of a particular application.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

Aspects, features, benefits and advantages of the embodiments will be apparent with regard to the following description, appended claims and accompanying drawings where:

FIG. 3 is a perspective view of an embodiment of a device in accordance with the principles of the present disclosure; and FIG. 4 is top view of the device shown in FIG. 3.

Like reference numerals indicate similar parts throughout the figures.

DETAILED DESCRIPTION

Figures 1, 2:
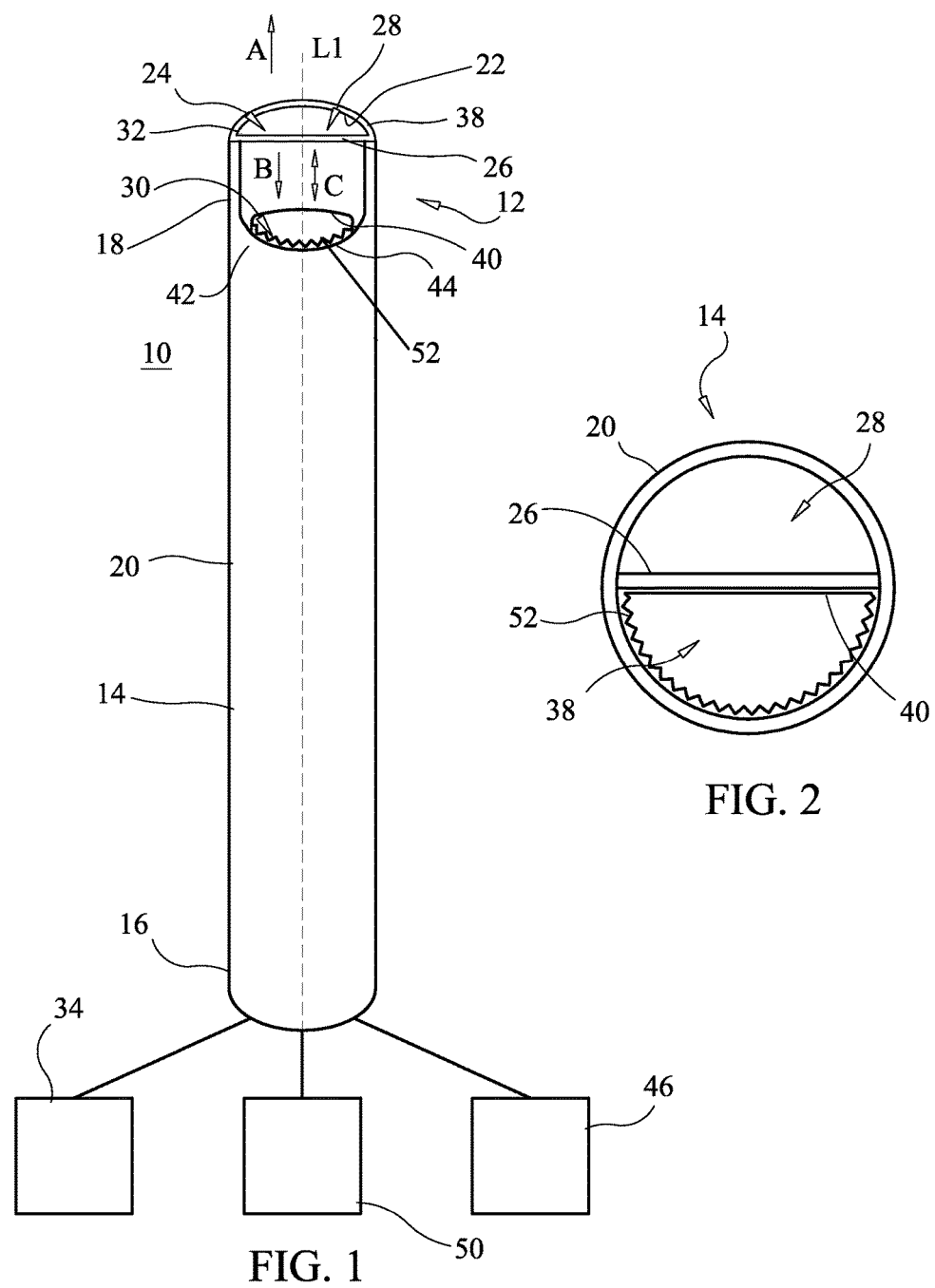
FIG. 1 is a perspective view of an embodiment of a device in accordance with the principles of the present disclosure.
FIG. 2 is top view of the device shown in FIG. 1.

Devices for efficient severing or cutting of a material or substance such as bone tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a more percutaneous approach which precisely removes just enough tissue (lamina or ligamentum flavum) to be effective without damaging the dura is being pursued.

In one embodiment, a bone shaving device is provided that employs an ultrasonic bone cutting edge that is safe to bypass nerve roots (due to a smooth and rounded surface) yet can still catch on hypertrophied facets lateral to the spinal canal. Longitudinal ultrasonic motion quickly and effectively shaves facet material in small passes, without the cutting edge physically contacting the dura of the spinal cord. In one embodiment, the cutting edge is undercut by 2 mm from the end of a tube, which allows for cutting only at the cutting edge. The serrated edge faces the facet and not the dura. In one embodiment, the cutting edge is piezo-driven. In one embodiment, the cutting edge is shielded from the dura to prevent vibrations from affecting the dura. In one embodiment, the cutting edge is not shielded from the drug such that vibrations may affect the dura. It is envisioned that the cutting edge can be variously configured and dimensioned, such as, for example, blunt, round or serrated, depending upon the requirements of a particular application.

In one embodiment, a secondary, small half-circular tube is disposed within one-half of a dual-lumen tube. The secondary tube alone is ultrasonically activated and piezo-driven to remove bone, leaving the larger tube relatively stationary and safe for the dura. In one embodiment, irrigation would be supplied through the longer distal lumen, and suction is provided to the shorter lumen to remove debrided bone material. In one embodiment, the dual-lumen tube is a stainless steel tube having a longer irrigation port and a shorter suction port. It is envisioned that all or only a portion of the primary tube, the secondary tube and/or the dual-lumen tube may have alternate cross section configurations, such as, for example, circular, semi-circular, oval, oblong, triangular, square, rectangular, polygonal, irregular, uniform, non-uniform, offset, staggered, and/or tapered, depending upon the requirements of a particular application.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

For purposes of the description contained herein, "vacuum" means pressure within a space that is lower by any amount than atmospheric or ambient pressure, and although not exclusive of a condition of absolute vacuum defined by a complete absence within a space of air, fluid or other matter, the term as used herein is not meant to require or be limited to such a condition.

Reference will now be made in detail to certain embodiments of the disclosure, examples of which are illustrated in the accompanying drawings. While the disclosure will be presented in conjunction with the illustrated embodiments, it will be understood that they are not intended to limit the invention to those embodiments. On the contrary, the disclosure is intended to cover all alternatives, modifications, and equivalents that may be included within the invention as defined by the appended claims.

The components of the surgical device can be fabricated from biologically acceptable materials suitable for medical apparatuses, including metals, synthetic polymers, ceramics, thermoplastic and polymeric material and/or their composites. For example, the components of the surgical device, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials.

In one embodiment, as shown in FIGS. 1-2, provided are components of a surgical system, such as, for example, a lumbar decompression system 10 in accordance with the principles of the present disclosure. System 10 includes an ultrasonic surgical device 12 for cutting tissue, such as, for example, bone tissue. Device 12 includes an elongated member, such as, for example, a circular tube 14 having a proximal end 16 and a distal end 18 spaced along a longitudinal axis L1. Tube 14 has an arcuate cross section configuration along its length. It is contemplated that tube 14 has alternate cross section configurations, such as, for example, oval, oblong, triangular, square, polygonal, irregular, uniform, non-uniform, offset, staggered, undulating, arcuate, variable and/or tapered. Tube 14 has a smooth and arcuate outer surface 20 so as to not damage surrounding healthy tissue. Tube 14 can be made out of stainless steel. It is contemplated that tube 14 is made out of various suitable materials, such as, for example, polyurethane, polyurea, polyether(amide), PEBA, thermoplastic elastomeric olefin, copolyester, and styrenic thermoplastic elastomer, steel, aluminum, titanium, nitinol, tungsten, molybdenum, metal alloys with high non-ferrous metal content and a low relative proportion of iron, carbon fiber, glass fiber, plastics, ceramics or a combination thereof. Tube 14 has a uniform outer diameter of approximately 1-5 mm along its length. In some embodiments, tube 14 is tapered from proximal end 16 to distal end 18.

Tube 14 includes an inner surface 22. Inner surface 22 defines a passageway 24 that extends between proximal end 16 and distal end 18. Passageway 24 has a circular cross section configuration. It is contemplated that passageway 24 has alternate cross section configurations, such as, for example, those alternatives described herein. Tube 14 includes a septum 26 positioned within passageway 24 such that septum 26 separates passageway 24 into a first passageway or conduit 28 and a second passageway or conduit 30. Septum 26 extends between the proximal and distal ends 16, 18 of tube 14 along longitudinal axis L1. In some embodiments, septum 26 extends between proximal end 16 and a portion of tube 14 proximal to distal end 18. Septum 26 has a substantially rectangular shape. It is contemplated that septum 26 is variously shaped, such as, for example, oval, circular, oblong, triangular, square, polygonal, irregular, uniform, non-uniform, offset, staggered, undulating, arcuate, variable and/or tapered depending on a particular application.

First conduit 28 extends between proximal end 16 and distal end 18 of tube 14. First conduit 28 includes an opening or outlet 32 disposed at its distal end 18. Proximal end 16 is attached to an irrigator or pump 34 that delivers irrigation fluid through first conduit 28, out of outlet 32 in the direction shown by arrow A in FIG. 1. The irrigation fluid is used to wash out the surgical site. The irrigation fluid may also facilitate suction of loose tissue fragments, and/or to cool ablated tissue. In some embodiments, proximal end 16 is attached to a vacuum 46 to produce suction at distal end 18 of tube 14 so as to remove tissue from the surgical site.

Distal end 18 of first conduit 28 has a substantially planar and smooth face 38 so as to not damage tissue. In some embodiments, planar face 38 may be polished. First and second conduits 28, 30 have a semi-circular cross section configuration along their length. It is contemplated that first and second conduits 28, 30 have various cross section configurations, such as, for example, round, oval, oblong, triangular, polygonal, irregular, uniform, non-uniform, consistent, variable, horseshoe shape, U-shape or kidney bean shape.

Second conduit 30 is configured for disposal of a cutting element, such as, for example, a cutting blade 40. Second conduit 30 extends between proximal end 16 of tube 14 to a distal end 42 that terminates before distal end 18 of first conduit 28 to form a stepped configuration. Distal end 42 of second conduit 28 is offset from distal end 18 of first conduit 28 by about 1-8 mm, preferably about 4 mm, such that distal end 42 of first conduit 28 shields healthy tissue from making contact with distal end 42 of second conduit 30. Distal end 42 of second conduit 30 includes an opening or an inlet 44 configured for aspirating the surgical site. Proximal end 16 of second conduit 30 is in fluid communication with a vacuum 46 to produce suction at inlet 44 in the direction shown by arrow B so as to remove tissue and fluids from the surgical site. In some embodiments, proximal end 16 is attached to a pump 48 that delivers irrigation fluid to inlet 44.

As discussed above, device 12 includes an ultrasonic-driven cutting element, such as, for example, blade 40. Blade 40 is disposed within second conduit 30. In one embodiment, blade 40 has a semicircular cross section along its length such that blade 40 is concentrically disposed within second conduit 30. It is contemplated that blade 40 has various cross section configurations, such as, for example, semicircular, have other cross-sectional shape, or simply be curved. Blade 40 extends from proximal end 16 to beyond distal end 42 of second conduit 30 such that blade 40 protrudes from inlet 44.

Blade 40 is configured for cutting tissue such that cutting blade 40 vibrates ultrasonically to cut tissue, such as, for example, bone. Blade 40 is driven by a motor, such as, for example, a piezoelectric motor 50 that ultrasonically vibrates blade 40 along longitudinal axis L1 within second conduit 30 and relative to tube 14 as shown by arrow C. Blade 40 is made to be a separate component from tube 14 so that first conduit 28 remains relatively stationary and experiences relatively little vibration as blade 40 vibrates ultrasonically. Reducing the ultrasonic vibration of first conduit 28 provides for greater protection to the dura and other surrounding tissues that come in contact with first conduit 28. Blade 40 defines a cutting edge 52 that is serrated and arcuately shaped. It is contemplated that edge 52 has various surface configurations and shapes, such as, for example, linear, straight, curved, convex, concave, continuous, intermittent, even, uneven and combinations thereof to facilitate cutting tissue.

In assembly, operation and use, system 10 is employed with a surgical procedure, such as, for example, a procedure to treat lateral lumbar spinal stenosis. In use, a medical practitioner obtains access to a surgical site in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area. Once access to the surgical site is obtained, the particular surgical procedure can be performed for treating the spine disorder.

A two-inch to five-inch long incision in the midline of the back is made, and the left and right back muscles are dissected off the lamina on both sides and at multiple levels. After the spine is accessed, device 12 is positioned in the surgical site and piezoelectric motor 50 is activated. Blade 40 is positioned in contact with a hypertrophied facet to debride or cut bone tissue while second conduit 28 protects lateral nerve roots and other surrounding healthy tissue from the ultrasonically vibrating cutting edge 52. The disintegrated bone tissue is then sucked or vacuumed through inlet 44 out of the surgical site. Pump 48 can also be activated during or after debriding the bone tissue to irrigate the surgical site and/or to facilitate shaven bone tissue into inlet 44.

In one embodiment, as shown in FIGS. 3-4, system 10 includes an ultrasonic surgical device 112, similar to device 12 described above. Device 112 includes an elongated member, such as, for example, a circular tube 114, similar to tube 114 described above. Tube 114 has a proximal end 116 and a distal end 118 spaced along a longitudinal axis L2. Tube 114 includes an inner surface 122 and an outer surface 120. Inner surface 122 defines a passageway 124, similar to passageway 24 described above. Passageway 124 has a circular cross section configuration. Tube 114 includes a septum 126, similar to septum 26 described above. Septum 126 is positioned within passageway 124 such that septum 126 separates passageway 124 into a first conduit 128 and a second conduit 130. Septum 126 extends between the proximal and distal ends 116, 118 of tube 114 along longitudinal axis L2. Septum 126 has a substantially rectangular shape that extends along the length of tube 114.

First conduit 128, similar to first conduit 28 described above, extends between proximal end 116 and distal end 118 of tube 114. First conduit 128 includes an opening or an outlet 132 disposed at its distal end 118. Proximal end 116 is attached to a pump 148 that delivers irrigation fluid through first conduit 128 and out of outlet 132 in the direction shown by arrow E. Distal end 118 of first conduit 128 has a substantially planar and smooth face 138 so as to not damage tissue.

First and second conduits 128, 130 have a semi-circular cross section configuration along their length. It is contemplated that first and second conduits 128, 130 have various cross section configurations, such as, for example, round, oval, oblong, triangular, polygonal, irregular, uniform, non-uniform, consistent, variable, horseshoe shape, U-shape or kidney bean shape.

Second conduit 130, similar to second conduit 30 described above, extends between proximal end 116 of tube 114 to a distal end 142 that terminates before distal end 118 of first conduit 128 to form a stepped configuration. Distal end 142 of second conduit 130 is offset from distal end 118 of first conduit 128 by about 1-3 mm, preferably about 2 mm, such that distal end 118 of first conduit 128 shields healthy tissue from making contact with distal end 142 of second conduit 130. Distal end 142 of second conduit 130 includes an opening or an inlet 144 configured for aspirating the surgical site. Proximal end 116 of second conduit 130 is in fluid communication with a vacuum 146 to produce suction at inlet 144 in the direction shown by arrow D so as to remove tissue and fluids from the surgical site.

Distal end 142 of second conduit 130 has an ultrasonic-driven cutting edge 152 configured for cutting tissue such that cutting edge 152 vibrates ultrasonically to cut tissue. Cutting edge 152 is ultrasonically driven by piezoelectric motor 150. In this embodiment, cutting edge 152 is integrated with tube 114 such that tube 114 ultrasonically vibrates with cutting edge 152 along the longitudinal axis as shown by arrow F. In one embodiment, cutting edge 152 is serrated and arcuately shaped. However, it is envisioned that cutting edge 152 may be variously configured and dimensioned such as, for example, blunt, round, planar, concave, polygonal, irregular, uniform, non-uniform, staggered, tapered, consistent or variable, depending on the requirements of a particular application.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for performing a surgical procedure, comprising:
    an elongated member having a proximal end, an opposite distal end, and a longitudinal axis extending through the proximal end and the distal end, the elongated member having an inner surface and an outer surface, the inner surface defining a passageway;
    a septum positioned within the passageway, the septum being configured to separate portions of the passageway into a first conduit and a second conduit, each of the first conduit and the second conduit having a longitudinal axis, the longitudinal axes of the first conduit and the second conduit being substantially aligned with the longitudinal axis of the elongated member, a distal end of the second conduit terminating before a distal end of the first conduit to form a stepped configuration, the distal end of the second conduit having an ultrasonic-driven cutting edge configured for cutting tissue such that the cutting edge vibrates ultrasonically to cut the tissue; and
    wherein a distal end of the first conduit includes an outlet configured for delivering material to a surgical site and the distal end of the second conduit includes an inlet configured for aspirating the surgical site.

2. The device as recited in claim 1, wherein the cutting edge is blunt.

3. The device as recited in claim 1, wherein the first conduit has a configuration that is different from a configuration the second conduit.

4. The device as recited in claim 1, wherein the septum extends between the proximal and distal ends of the elongated member.

5. The device as recited in claim 1, wherein a proximal end of the second conduit is attached to a vacuum to produce suction at the inlet so as to remove tissue from a surgical site.

6. The device as recited in claim 5, wherein a proximal end of the first conduit is attached to a pump that delivers irrigation fluid to the outlet.

7. The device as recited in claim 1, wherein the cutting edge is at least in part arcuate.

8. The device as recited in claim 1, wherein the cutting blade extends beyond the distal end of the second conduit such that the cutting blade protrudes from the inlet.

9. The device as recited in claim 1, wherein the elongated member has a substantially tubular configuration, and the outer surface is substantially smooth.

10. The device as recited in claim 1, wherein the elongated member is substantially circular and the first conduit has a configuration that is different from a configuration of the second conduit.

11. A device for performing a surgical procedure, comprising:
    a tubular member having a proximal end, an opposite distal end, a length extending from the proximal end and the distal end, and a longitudinal axis extending through the proximal end and the distal end, the tubular member having an inner surface and an outer surface, the inner surface defining a passageway;
    a septum positioned within the passageway, the septum being configured to separate portions of the passageway into a first conduit and a second conduit, the first conduit and the second conduit being on opposite sides of the septum, each of the first conduit and the second conduit having a longitudinal axis, the longitudinal axes of the first conduit and the second conduit being substantially aligned with the longitudinal axis of the tubular member, a distal end of the second conduit terminating before a distal end of the first conduit to form a stepped configuration, the distal end of the second conduit having an ultrasonic-driven cutting edge configured for cutting tissue such that the cutting edge vibrates ultrasonically to cut the tissue; and
    wherein a distal end of the first conduit includes an outlet configured for delivering material to a surgical site and the distal end of the second conduit includes an inlet configured for aspirating the surgical site.

12. The device as recited in claim 11, wherein the cutting edge is blunt.

13. The device as recited in claim 11, wherein the first conduit has a configuration that is different from a configuration the second conduit.

14. The device as recited in claim 11, wherein the septum extends between the proximal and distal ends of the tubular member.

15. The device as recited in claim 11, wherein a proximal end of the second conduit is attached to a vacuum to produce suction at the inlet so as to remove tissue from a surgical site.

16. The device as recited in claim 15, wherein a proximal end of the first conduit is attached to a pump that delivers irrigation fluid to the outlet.

17. The device as recited in claim 11, wherein the cutting edge is at least in part arcuate.

18. The device as recited in claim 11, wherein the cutting blade extends beyond the distal end of the second conduit such that the cutting blade protrudes from the inlet.

19. The device as recited in claim 11, wherein the tubular member is substantially circular and the first conduit has a configuration that is different from a configuration of the second conduit.

20. A device for performing a surgical procedure, comprising:
- a tubular member having a proximal end, an opposite distal end, a length extending from the proximal end and the distal end, and a longitudinal axis extending through the proximal end and the distal end, the elongated member having an inner surface and an outer surface, the inner surface defining a passageway extending between the proximal end and the distal end;
- a septum positioned within the passageway, the septum being configured to divide portions of the passageway into a first conduit and a second conduit, each of the first conduit and the second conduit having a longitudinal axis, the longitudinal axes of the first conduit and the second conduit being substantially aligned with the longitudinal axis of the tubular member, a distal end of the second conduit terminating before a distal end of the first conduit to form a stepped configuration, the distal end of the second conduit having an ultrasonic-driven cutting edge configured for cutting tissue such that the cutting edge vibrates ultrasonically to cut the tissue, the ultrasonic-driven cutting edge being at least in part arcuate; and
- wherein a distal end of the first conduit includes an outlet configured for delivering material to a surgical site and the distal end of the second conduit includes an inlet configured for aspirating the surgical site, and wherein a proximal end of the first conduit is attached to a pump that delivers irrigation fluid to the outlet and a proximal end of the second conduit is attached to a vacuum to produce suction at the inlet so as to remove tissue from a surgical site.

* * * * *

UNITED STATES PATENT AND TRADEMARK OFFICE
CERTIFICATE OF CORRECTION

PATENT NO. : 10,143,486 B2
APPLICATION NO. : 15/043657
DATED : December 4, 2018
INVENTOR(S) : Craig E. Lauchner Page 1 of 1

It is certified that error appears in the above-identified patent and that said Letters Patent is hereby corrected as shown below:

In the Specification

In Column 1, Line 7, delete "2013," and insert -- 2013, now Pat. No. 9,289,227, --, therefor.

In Column 4, Line 52, delete "the drug" and insert -- the dura --, therefor

In Column 7, Line 40, delete "second conduit 28" and insert -- second conduit 30 --, therefor.

In Column 8, Line 34, delete "second conduit 28" and insert -- second conduit 30 --, therefor.

In the Claims

In Column 10, Lines 4-5, in Claim 3, delete "configuration the" and insert -- configuration of the --, therefor.

In Column 10, Lines 57-58, in Claim 13, delete "configuration the" and insert -- configuration of the --, therefor.

Signed and Sealed this
Ninth Day of July, 2019

Andrei Iancu
*Director of the United States Patent and Trademark Office*